(12) United States Patent
Stein et al.

(10) Patent No.: US 10,335,560 B2
(45) Date of Patent: Jul. 2, 2019

(54) SINGLE HIGH DOSE DRY-POWDER INHALER AND METHOD

(71) Applicant: 3M INNOVATIVE PROPERTIES COMPANY, Saint Paul, MN (US)

(72) Inventors: Stephen W. Stein, Lino Lakes, MN (US); Zhaolin Wang, Nanjing (CN)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 619 days.

(21) Appl. No.: 14/914,428

(22) PCT Filed: Aug. 26, 2014

(86) PCT No.: PCT/US2014/052632
§ 371 (c)(1),
(2) Date: Feb. 25, 2016

(87) PCT Pub. No.: WO2015/034709
PCT Pub. Date: Mar. 12, 2015

(65) Prior Publication Data
US 2016/0199596 A1    Jul. 14, 2016

Related U.S. Application Data

(60) Provisional application No. 61/873,530, filed on Sep. 4, 2013.

(51) Int. Cl.
*A61M 11/00* (2006.01)
*A61M 15/00* (2006.01)

(52) U.S. Cl.
CPC .... *A61M 15/0005* (2014.02); *A61M 15/0021* (2014.02); *A61M 15/0028* (2013.01);
(Continued)

(58) Field of Classification Search
CPC .............. A61M 15/0005; A61M 15/02; A61M 15/0021; A61M 15/0028; A61M 15/0043; A61M 15/0091
See application file for complete search history.

(56) References Cited

U.S. PATENT DOCUMENTS 5,187,921 A * 2/1993 Wilson .................. B26D 1/245
141/1
5,408,994 A     4/1995 Wass
(Continued)

FOREIGN PATENT DOCUMENTS

CN   101965208 A   2/2011
JP   11-510412     9/1999
(Continued)

OTHER PUBLICATIONS

Ext_EP_Search_Report_EP14841987.2 dated Feb. 7, 2017.
(Continued)

*Primary Examiner* — Kathryn E Ditmer (57) ABSTRACT

A dry-powder inhaler comprising a housing comprising at least one air inlet to a first air passage and a second air passage extending from the first air passage and terminating in a mouthpiece; the housing thereby providing a continuous air passage through the at least one air inlet, the first and second air passages, and the mouth piece; a rigid, fixed, powdered-medicament reservoir comprising a base, the reservoir being associated with the first air passage, and together with the first air passage forming a powder chamber; wherein air passing through the powder chamber travels substantially parallel to an upper surface of the reservoir and powdered-medicament positioned on the base in the reservoir, the upper surface of the reservoir having a surface area, and the reservoir having a volume.

20 Claims, 5 Drawing Sheets

(52) U.S. Cl.
CPC ....... *A61M 15/0091* (2013.01); *A61M 11/002* (2014.02); *A61M 15/0043* (2014.02); *A61M 2202/064* (2013.01); *A61M 2202/066* (2013.01); *A61M 2206/10* (2013.01); *A61M 2209/02* (2013.01)

(56) References Cited

U.S. PATENT DOCUMENTS

| | | | |
|---|---|---|---|
| 5,437,271 | A | 8/1995 | Hodson |
| 5,469,843 | A * | 11/1995 | Hodson ............. A61M 15/0045 128/203.12 |
| 5,482,032 | A | 1/1996 | Smith |
| 5,582,162 | A * | 12/1996 | Petersson .......... A61M 15/0045 128/203.12 |
| 5,655,523 | A | 8/1997 | Hodson |
| 6,102,035 | A | 8/2000 | Asking |
| 6,220,243 | B1 | 4/2001 | Schaeffer |
| 6,622,723 | B1 * | 9/2003 | Nilsson ............. A61M 15/0045 128/203.12 |
| 6,626,173 | B2 | 9/2003 | Genova |
| 6,722,364 | B2 | 4/2004 | Connelly |
| 6,923,178 | B2 | 8/2005 | Snow |
| 7,556,035 | B2 | 7/2009 | Young |
| 2002/0092523 | A1 | 7/2002 | Connelly |
| 2004/0206773 | A1 * | 10/2004 | Ede ........................ A61J 1/035 222/83 |
| 2005/0183723 | A1 * | 8/2005 | Pinon ................. A61M 15/0065 128/203.15 |
| 2008/0197045 | A1 * | 8/2008 | Metzger ............ A61M 15/0045 206/539 |
| 2009/0084379 | A1 * | 4/2009 | Goeckner ......... A61M 15/0028 128/203.15 |
| 2010/0051027 | A1 * | 3/2010 | Remmelgas ...... A61M 15/0045 128/203.15 |
| 2012/0132203 | A1 | 5/2012 | Hodson |

FOREIGN PATENT DOCUMENTS

| | | | |
|---|---|---|---|
| WO | WO 1997/05918 | 2/1997 | |
| WO | WO 2007042822 A2 | 4/2007 | |
| WO | WO 2009/082343 | 7/2009 | |
| WO | WO 2009082341 A1 | 7/2009 | |
| WO | WO-2010021589 A1 * | 2/2010 | ........ A61M 15/0028 |
| WO | WO 2011-023947 | 3/2011 | |
| WO | WO 2012-050945 | 4/2012 | |

OTHER PUBLICATIONS

Nichols, "New Approaches to Optimizing Dispersion in Dry Powder Inhalers—Dispersion Force Mapping and Adhesion Measurements", Respiratory Drug Delivery, 2008, vol. 1, pp. 175-184.
International Search Report for PCT International Application No. PCT/US2014/52632, dated Dec. 22, 2014, 4pgs.

* cited by examiner

SINGLE HIGH DOSE DRY-POWDER INHALER AND METHOD

CROSS REFERENCE TO RELATED APPLICATIONS

This application is a national stage filing under 35 U.S.C. 371 of PCT/US2014/052632, filed Aug. 26, 2014, which claims the benefit of U.S. Provisional Application No. 61/873,530, filed Sep. 4, 2013, the disclosures of which are incorporated by reference in their entirety herein.

BACKGROUND

Asthma and other respiratory diseases have been treated by the inhalation of appropriate medicaments. For many years the two most widely used and convenient choices of treatment have been the inhalation of medicament from a drug solution or suspension in a pressurized metered dose inhaler (pMDI), or inhalation of powdered drug, generally admixed with an excipient, from a dry powder inhaler (DPI). Following concern about a link between depletion of the earth's ozone layer and chlorofluorocarbon (CFC) emissions, interest in DPI systems has increased.

Most DPIs use either bulk powder reservoirs or individual pre-measured doses. In general, DPIs include an air passage leading from a dispensing chamber and terminating in a port for inserting into the users mouth or nasal passage. Inhalation at the port brings air through the dispensing chamber, carrying particles of medicament into the lungs of the user. Development efforts in this area have focused primarily on problems associated with accurately metering a measured small quantity (e.g. 500 micrograms or less) of powder either from a bulk reservoir within an inhaler or from a capsule or blister. In some instances such as with potent drugs, excipients such as lactose powder have been added, increasing the quantity of powder for accurate metering or for other reasons to up to, for example, at least 1 milligram. Such excipients may be undesirable as they can pose subsequent powder agglomeration or deagglomeration problems and can cause dryness and other unwanted effects in the patient's mouth. Traditional DPIs require carrier excipients, such as lactose, which dilute out the effective dose and increase the total mass of formulation needed.

One example of dry powder inhalers includes those in which predetermined doses of medicament are dispensed from a sheet material including discrete microdepressions (having a depth of about 5 to 500 microns and an opening at the surface of the sheet material of about 10 to 500 microns in width) filled with medicament. DPIs of this nature are disclosed in U.S. Pat. Nos. 5,408,994, 5,437,271, 5,469,843, 5,482,032, and 5,655,523.

However, there continues to be an interest and need for improved DPIs, which provide, for example, greater patient comfort and effectiveness and/or improved dosing capability.

SUMMARY

It has now been found that a single high dose of a respirable drug can be delivered to a patient's lungs with a dry powder inhaler, a high dose being greater than 5 milligrams, preferably greater than 10 milligrams of micronized drug powder.

Accordingly there is provided a dry-powder inhaler comprising:

a housing comprising at least one air inlet to a first air passage and a second air passage extending from the first air passage and terminating in a mouthpiece; the housing thereby providing a continuous air passage through the at least one air inlet, the first and second air passages, and the mouth piece;

a rigid, fixed, powdered-medicament reservoir comprising a base, the reservoir being associated with the first air passage, and together with the first air passage forming a powder chamber;

wherein air passing through the powder chamber travels substantially parallel to an upper surface of the reservoir and substantially parallel to powdered medicament positioned on the base in the reservoir, the upper surface of the reservoir having a surface area, and the reservoir having a volume, the surface area being at least 1 cm$^2$, and the surface area to volume ratio being at least 1 cm$^{-1}$ and not more than 10 cm$^{-1}$; and wherein the dry-powder inhaler has a single respirable-dose delivery capability of at least 5 mg of the powdered medicament.

In one embodiment, the reservoir and powder chamber are elongated along a long axis which is parallel to the flow of air through the first passage; and wherein the reservoir has a length along the long axis and a width perpendicular to the long axis, wherein the length and width define a length/width aspect ratio of at least 2.5.

In another embodiment, the powdered-medicament reservoir has a volume of 0.01 ml to 5 ml.

In another embodiment, the upper surface of the reservoir is spaced a distance of at least 1 mm and not more than 3 mm from a top surface of the first air passage.

In another embodiment, the dry-powder inhaler further comprises a plurality of entrainment-modulating structures in contact with the powdered medicament in the reservoir.

In another embodiment, during an inhalation the amount of powdered medicament which can be removed from the reservoir during the first 0.5 seconds of air passing through the inhaler is limited to not more than 80% of the total powder removed during the entire inhalation, preferably not more than 60%, more preferably not more than 40%, most preferably not more than 20%.

In another embodiment, the dry-powder inhaler further comprises a deagglomerator associated with the second air passage, associated with the powder chamber, or associated with both the second air passage and the powder chamber and comprising a portion of the continuous air passage.

In a further embodiment, the powdered-medicament reservoir is removable and replaceable.

In a further embodiment, the powdered-medicament reservoir includes a removable seal covering the powder in the reservoir prior to use.

In another aspect, there is provided a method of delivering a single high dose of a powdered medicament to a patient, the method comprising the steps of:

providing the dry-powder inhaler as described above or according to any embodiment described herein; and having a patient inhale through the mouthpiece of the inhaler;

wherein the patient receives a respirable dose of at least 5 mg of the powdered medicament.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Definitions

The following terms are used herein according to the following definitions.

The term "substantially parallel" refers to the direction of air passing over the reservoir and through the inhaler without being directed into the reservoir or into powdered medicament in the reservoir. The air passes over the powder bed in a direction parallel to the surface of the powder bed, and has contact with the powder bed surface while passing over the surface. The powder bed is the powdered medicament positioned on the base in the reservoir, with the powdered medicament distributed across the length and width of the reservoir.

The term "fine particle dose" is used interchangeably with "respirable dose", which refers to the amount of powdered medicament delivered from the dry-powder inhaler, which is of sufficiently small particle size to be inhaled into the human lung. Such small particles may have an aerodynamic diameter of less than about 5 micrometers.

The term "rigid" as used herein refers to a powdered-medicament reservoir which is not a thin film or sheet material and which does not deform during use of the dry-powder inhaler.

The term "fixed" as used herein refers to a powdered-medicament reservoir which is stationary with respect to the dry-powder inhaler housing and the first air passage with which the reservoir is associated during use of the dry-powder inhaler. During use means while the user is inspiring air through the inhaler or the inhaler is being tested on a fine particle dose estimator apparatus.

As used herein, "a," "an," "the," "at least one," and "one or more" are used interchangeably. The term "and/or" means one or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF ILLUSTRATIVE EMBODIMENTS

The presently provided dry-powder inhaler is configured so that air passing through the powder chamber travels substantially parallel to the upper surface of the reservoir and of the powdered medicament positioned on the reservoir's base. In this way, entrainment of the powder is only possible from the surface of the medicament as the air passes over the surface, thereby holding up or reducing the entrainment rate of the powder. In so doing, the powder may be removed from the reservoir and entrained during a greater portion of the entire inspiration of the user, for example, at least 0.5 seconds, one second, two seconds or even up to four seconds, enabling delivery of a high dose of medicament while minimizing the concentration of particulate within the air stream. Advantageously, increased patient comfort may be provided, because oral intake of the medicament is spread over a relatively longer period of time, thereby minimizing or avoiding coughing or choking due to the large medicament dose.

This is in contrast with known configurations in which the air is forced into the surface of the powder or into the bulk of the powder in order to entrain all of the powder, typically in a very short time frame, for example, within a fraction of one second such as about 0.1 or 0.2 seconds. In another example, where a longer time frame is contemplated, an inhaler for administering a pharmaceutical composition during a prolonged time period is reported in U.S. Pat. No. 6,622,723, wherein a dosing element having an adapted opening moves along an extended dose arrangement of a dosing member during administration to prolong the time period during which the pharmaceutical composition is released from the dosing member into an air stream of the inhaler during an inspiration of one to two seconds. This example suffers from the disadvantages of being complex to manufacture because of the moving parts and may not be capable of delivering the high respirable dose provided by the presently provided inhaler which utilizes a fixed reservoir and housing without moving parts.

The presently provided dry-powder inhaler is also configured so that the upper surface of the reservoir, which is the surface exposed to the air, has a surface area of at least 1 $cm^2$. The powdered medicament is positioned in the reservoir and on the reservoir base, preferably with the powder evenly distributed in the reservoir and over the base of the reservoir. When the level of the powder in the reservoir is at the same level as the top surface of the reservoir, the exposed area of the powdered-medicament dose (not the area of the particle surfaces) is equal to the upper surface area of the reservoir. For certain embodiments, preferably the upper surface area of the reservoir is at least 1.2, 1.5, or 1.7 $cm^2$. For certain of these embodiments, the upper surface area of the reservoir is not more than 5, 4, 3.5, 3, or 2.5 $cm^2$. For certain of these embodiments, preferably the upper surface area of the reservoir is 1.5 to 3 $cm^2$, more preferably 1.5 to 2.5 $cm^2$, most preferably 1.7 to 2.5 $cm^2$.

The reservoir has a volume, which can be calculated based upon the geometry of the reservoir or which can be conveniently measured by filling the reservoir with a liquid, such as water, and then measuring the volume of the liquid required to fill the reservoir at room temperature, such as 23° C. For certain embodiments, preferably the powdered medicament fills the reservoir to within 50%, 75%, 80%, 90%, or 100% of the volume of the reservoir.

The reservoir has a surface area to volume ratio (surface area/volume) of at least 1 $cm^{-1}$ and, preferably, not more than 10 cm$^{-1}$. For certain embodiments, preferably the reservoir has a surface area to volume ratio of at least 2 cm$^{-1}$, more preferably at least 3 cm$^{-1}$, and most preferably at least 4 cm. For certain of these embodiments, the reservoir has a surface area to volume ratio of not more than 10 cm$^{-1}$, 9 cm$^{-1}$, or 8 cm$^{-1}$. For certain of these embodiments, preferably the reservoir has a volume of at least 0.01 ml, preferably at least 0.1 ml, more preferably at least 0.2 ml. For certain of these embodiments, the reservoir has a volume of not more than 5 ml, preferably not more than 2 ml, and more preferably not more than 0.5 ml.

Applicants have found that the provided surface area enables the controlled entrainment described above, with the inspired air moving parallel to the surface of the reservoir and the powdered medicament therein, and at the same time the provided reservoir volume is sufficient to yield the high respirable dose of medicament.

Applicants have found that previously known dry-powder inhalers failed on the one hand to provide sufficient reservoir and powdered medicament area exposed to the air or on the other hand to provide sufficient powdered medicament volume with sufficient exposed area in order to deliver the presently required high dose but with the slower release of the powdered medicament from the reservoir into the inspired air. One example of this is shown in comparative Example 1 wherein a conventional reservoir with a "well" configuration was used. This had a surface area of 0.8 cm$^2$ and delivered a respirable dose of only 1.9 mg of powdered medicament with a very high rate of release from the conventional reservoir into the inspired air.

For certain embodiments, preferably the reservoir and powder chamber are elongated along a long axis which is parallel to the flow of air through the first passage. The reservoir and powder chamber have a length along the long axis and a width perpendicular to the long axis. The length and width are parallel to the upper surface of the reservoir (and the powdered medicament in the reservoir), and the length and width defining a length/width aspect ratio of at least 2.5. It has now been found that this configuration helps reduce the rate at which the powder is entrained in the air stream, keeping the particle concentration relatively low as described above. This contributes to particle deagglomeration and may help reduce agglomeration, which is difficult to achieve with a conventional reservoir, since such reservoirs generally produce a single, very large bolus of the powdered medicament. The presently provided length/width aspect ratio further provides more time with the inspired air traveling parallel to the surface of the reservoir and powder, resulting in a lower concentration of powder but with the high powder dose. For certain of these embodiments, preferably the length/width aspect ratio of the reservoir is at least 3, 3.5, or 4. This aspect ratio is preferably not more than 10.

For certain embodiments, preferably the top surface of the reservoir is spaced a distance of at least 1 mm and not more than 3 mm from a top surface of the first air passage. It has been found that this dimension provides sufficient space for the inspired air to move through the powder chamber, and pass over and entrain the powdered medicament without causing an excessively high pressure drop.

For certain embodiments, preferably the dry-powder inhaler further comprises a plurality of entrainment-modulating structures in contact with the powdered medicament in the reservoir. The powered medicament partially or fully covers the structures. Such structures can reduce the rate at which the drug powder becomes entrained from the reservoir. This can help prevent the reservoir from being emptied of powdered medicament too quickly, thereby allowing the powder to be spread out over a larger volume of air passing through the powder chamber. This reduces the concentration of medicament in the inspired air to produce the results described above. For certain of these embodiments, the entrainment-modulating structures emerge from the base of the reservoir, although such structures could additionally or instead emerge from the top of the first air passage directly above the reservoir and powdered medicament. The entrainment-modulating structures can be any structures positioned within the powder chamber which reduce the rate of powder entrainment. This helps prevent an excessively high rate of removal of powdered medicament from the reservoir and powder chamber. Preferably, for certain embodiments, the entrainment-modulating structures are selected from the group consisting of posts, paddles, baffles, walls parallel to air flow, and a combination thereof.

Posts can be cylindrical structures in the reservoir. For certain embodiments, the posts may having a length no greater than 100, 90, 80, 70, 60, or 50 percent the height of the reservoir as measured from the base of the reservoir where the post begins to the top edge of the reservoir. For certain embodiments, the posts have a length at least 20, 30, or 40 percent the height of the powder chamber as measured from the base of the reservoir where the post begins to the top of the first air passage. For certain embodiments, preferably posts have a height no greater than 100, 98, 95, 90, or 80 percent the height and for certain embodiments at least 30, 40, 50, or 75 percent the height of the reservoir as measured from the base of the reservoir where the post begins to the top edge of the reservoir. For certain embodiments, such posts may have a diameter of at least 5, 10, 20, or 30 percent the width of the reservoir and for certain embodiment not more than 50, 40, 30, or 20 percent the width of the reservoir. For certain embodiments, the entrainment-modulating structures are posts.

Paddles are horizontally elongated post-like structures wherein the structures are elongated in the direction of the air flow. Paddles may have a height and width (thickness) as described above for the post structure's height and diameter, respectively. The elongated direction of the paddles may have a dimension of at least 2 times the width of the paddles and in certain embodiments up to 5 or 10 times the width of the paddles.

Baffles are structures which traverse at least a portion of the width of the reservoir. In certain embodiments, baffles are structures as described above for the paddles, but where the elongated direction is now perpendicular to the flow of air. In this case the baffles traverse only a portion of the width of the reservoir. In other embodiments, the baffles traverse the entire width of the reservoir, forming a series of small reservoirs, for example at least 3, 4, 5, 6, or 7 small reservoirs, and in certain embodiments up to 15 or 10 small reservoirs.

Walls parallel to air flow may be straight or curved. The walls or ridges form a series of channels which run parallel with the direction of the air flow and extend at least 50, 60, 70, 80, 90, or 100 percent of the length of the reservoir. The ridges or walls may have a height and width (thickness) as described above for the post structure's height and diameter, respectively. For certain embodiments, the reservoir comprises at least 1, 2, 3, or 4 walls forming at least 2, 3, 4, or 5 channels, and for certain embodiments up to 20, 10, or 5 walls forming the corresponding channels. For certain embodiments, the width of each channel is at least 2, 5, 10, 20, 25, 30, or 40 percent the width of the reservoir. Preferably the width of each channel is not more than 40 or 30 percent of the width of the reservoir. The width of each channel is measured from the center of each ridge or wall forming the channel or from the center of a ridge or wall to the top edge of the reservoir forming the channel.

Entrainment-modulating structures as described above may, in certain embodiments, occupy less than 75%, 50%, 25%, or 10% the volume of the reservoir in which they are included. The structures may be arranged randomly or in a geometric pattern(s); arranged in single or multiple rows with rows either aligned or staggered, straight or curved. The structures can be about the same height or have variable heights. The structures within a reservoir can be present in a single shape or in two or more shapes. Shapes can be symmetrical (having a point, line, or plane of symmetry) or unsymmetrical. Individual structures can contain holes, cut-outs, or voids; and can have smooth or structured surfaces (including bumps, depressions such as dimples, or the like). Individual structures can be tapered, flared, or angled at the base (for example posts tapered, flared, or angled at the base). Individual structures can be in a shape of cones or pyramids (with pointed or truncated tips) or dome shaped. Cylindrical posts can be of any geometric shape including circle, oval, triangle or wedge, square, rectangle, trapezoid, polygon having 3 to 10 sides, diamond, star, hourglass, dumbbell, teardrop, crescent, and waveform. Individual structures can have an amorphous shape with convex and/or concave features. The edges of individual structures can be straight or rounded and the ends of individual structures can be flat, rounded, or pointed, or a combination thereof.

As indicated above, the dry-powder inhaler is configured so as to limit the rate at which the powered medicament is entrained into the inspired air, thereby keeping the concentration of particles in the inspired air low while dispensing a high dose of respirable medicament. In one embodiment, during an inhalation the amount of powdered medicament which can be removed from the reservoir during the first 0.5 seconds of air passing through the inhaler is limited to not more than 80% of the total powder removed during the entire inhalation, preferably not more than 60%, more preferably not more than 40%, most preferably not more than 20%. For certain of these embodiments, these limits are achieved during the first 1 second of air passing through the inhaler.

Powders of a respirable particle size range tend to be highly cohesive and readily form particle agglomerates. Such particles may be too large to be inhaled into the lungs of a subject, but become trapped in the oral cavity or other areas through which the inspired air must travel on its way to the lungs. This may pose a challenge in configuring dry-powder inhalers, which may be addressed by including a deagglomerator section that imparts energy into the powder to deagglomerate the agglomerates to a size (preferably the size of the primary particles, e.g., aerodynamic diameter less than about 5 microns) capable of penetrating into the lung.

For certain embodiments, preferably a deagglomerator is associated with the second air passage, with the powder chamber, or with both the second air passage and the powder chamber. As such, the deagglomerator comprises a portion of the continuous air passage down-stream from the reservoir. The deagglomerator may cause deagglomeration of the powder by impacting the agglomerates against a surface of the dry-powder inhaler, against other particles contained in the powder, or a combination thereof.

Deagglomerators that cause the powder to impact at high velocity onto surfaces of a dry-powder inhaler device have been shown to be more effective at deagglomerating the powder into a respirable particle size. Applicants have found that this poses a challenge for high dose dry-powder inhalers, since the large amount of powder delivered causes the deagglomerator to be overwhelmed with powder resulting in increased particle-to-particle impaction, reduced particle-to-surface impaction, and concomitant decrease in deagglomerator efficiency. In order to maximize the efficiency of deagglomerators used for high dose dry-powder inhaler applications, Applicants found that it would be desirable to have the powder contained in a reservoir configured so that the powdered medicament is slowly released into the airflow as described above, such that the deagglomerator is not overwhelmed with powder and the amount of particle-to-surface impaction occurring is maximized. As such, Applicants have found that associating the presently provided reservoir and powder chamber configuration with a deagglomerator advantageously increases the effectiveness of the deagglomerator.

For certain embodiments, preferably the deagglomerator is at particle-to-surface impaction deagglomerator. For certain of these embodiments, the deagglomerator is at least one S-shaped channel. The S-shaped channel includes at least two bends, the second bend being of opposing or reverse-handedness to that of the first bend, thereby forming an "S" bend. The S-shaped channel incorporates two or more bends, each of from 35° to 180°. The radius of curvature of the center of the bends is preferably no greater than 10 mm.

The S-shaped channel may have a uniform cross-section throughout its length. However, for certain embodiments, preferably the S-shaped channel has a cross-sectional area that varies along a longitudinal axis of the channel, the cross-sectional area being perpendicular to the longitudinal axis. The longitudinal axis is defined by the path that inspired air travels through the channel. Preferably, for certain embodiments, the channel includes at least one convergence and one divergence corresponding to a cross-sectional area decrease of about 15 to about 35 percent and a cross-sectional increase of about 15 to about 35 percent, respectively.

The S-shaped deagglomeration channel may be incorporated at any point in the continuous air passage between the powder chamber and the mouthpiece. Preferably, this channel is positioned at or near the mouthpiece in order to minimized pressure drops. Certain S-shaped deagglomerators are further described in U.S. Pat. No. 5,469,843.

As indicated above, the presently provided dry-powder inhaler can produce a single respirable dose of at least 5 mg. However, Applicants have achieved significantly higher respirable doses with the present inhaler, for example, at least 10 mg or more of powdered medicament. The presently provided dry-powder inhaler may provide reproducible single respirable doses. A maximum respirable dose of powdered medicament of not more than 100 mg, 75 mg, 60 mg, 50 mg, 40 mg, 35 mg, 25 mg, or 20 mg may be provided by the present dry-powder inhaler.

For certain embodiments, preferably the present dry-powder inhaler can provide a fine particle fraction of at least 10%, more preferably at least 15%, most preferably at least 20%, 30% or even 50%. The fine particle fraction is the respirable dose divided by the loaded dose, the loaded dose being the amount of powdered medicament positioned in the reservoir prior to use.

For certain embodiments, the powdered-medicament reservoir is removable and replaceable. This allows the patient to reuse the dry-power inhaler housing by simply removing the spent reservoir and installing an unused reservoir containing the powdered medicament onto the housing.

In order to protect the medicament from air, water, and other elements which might degrade and agglomerate the powdered medicament, for certain embodiments, preferably the powdered-medicament reservoir is sealed at the upper surface of the reservoir. Preferable the seal is in the form of a peelable film that has a flap or tab which extends outside of the air inlet of the device. The user can grasp the flap or tab and pull to peel the film from the surface of the reservoir, thereby exposing the powder in the reservoir to the air passage and to inspired air when the user inhales through the inhaler mouthpiece. The sealable film may be a polymeric film or a metal (e.g., aluminum) foil laminate with low water and oxygen permeability. The sealable film may be sealed to the top of the reservoir edges with a heat or pressure sealable film, an adhesive, or the like.

Any drug which may be made into a fine powder form and which is effective when applied as a particulate to oral, nasal, bronchial, and lung tissue may be used. However, drugs which may be more effective when applied at the higher doses provided by the present dry-powder inhaler include antibiotics such as tobramycin, colistin, colistin sulphomethate, gentamicin, colomycin, denufosol tetrasodium, aztreonam lysine, duramycin, pentamidine isethionate, zanamivir, ribavirin, amphotericin B, capriomycin sulfate, rifampicin, and doxycycline; cromolyn sodium; and terbutaline. Other drugs which may be suitably used in the present dry-powder inhaler include antiallergics including nedocromil, flu treatments including relenza (zanamivir), macrolide antibiotics including tacrolimus, diuretics including amiloride, PDE4 inhibitors including CHF6001 and BAY19-8004, leukotriene antagonists, monoclonal antibodies, insulin, DNAse including pulmozyme, and proteins and peptides including somatropin, IL-2, IL-11, lepirudin, clancreept, and leneeteplase. Further drugs which may be suitably delivered by the present dry-powder inhaler are described in International Publication No. WO 2012/050945.

The powdered medicament may be comprised of crystalline, micronized particles of a single active pharmaceutical ingredient (API), amorphous particles of a single API, a mixture containing particles of two or more APIs wherein individual particles consist of a single API, engineered powders in which the particles consist of both excipient and one or more APIs, and powder blends containing API particles and excipient (e.g., lactose) particles. In order to dispense a high dose of a single API, for certain embodiments, preferably the powder consists of only medicament.

Figure 1:
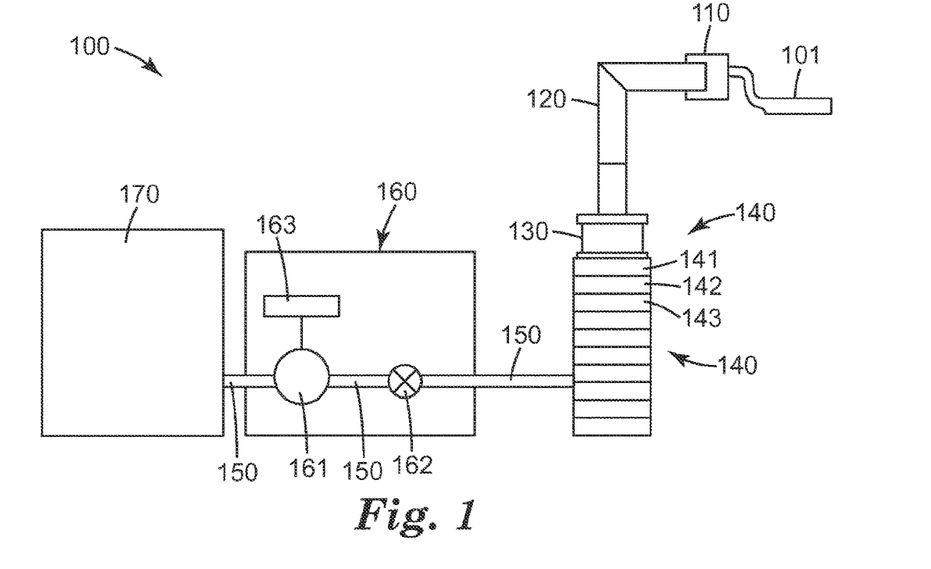
FIG. 1 is a schematic of a fine particle dose estimation apparatus used in the present Examples.

Reference is now made to the accompanying drawings. FIG. 1 is a schematic view of fine particle dose estimation apparatus 100, which was used to determine the respirable dose provided by dry-powder inhalers in the present Examples. The mouthpiece of test dry-powder inhaler 101 is coupled to USP inlet 120 via coupler 110 without air leaks between coupler 110 and the mouthpiece and between coupler 110 and USP inlet 120. Inlet 120 is mounted on a modified Andersen Mark-II Cascade Impactor (ACI) 140 via pre-separator 130, rated for 60 liters per minute of air. Pre-separator 130 is coupled to ACI Stage 1 (142) via modified ACI Stage 0 (141). Stage 0 (141) was modified by machining out the interior thin portion of the stage that contained all of the impaction nozzles, making stage 0 (141) merely an external shell to which both pre-separator 130 and stage 1 (142) are coupled. No impaction plate was placed under stage 0 (141), so that air passing through pre-separator 130 flows directly to the impaction nozzles of stage 1 (142). An impaction plate (not shown) is included under stage 1 (142) to collect large particles, which are considered to be primarily agglomerated particles. In use, the inside of USP inlet 120 and the impaction plate were coated with 50:50 glycerol/methanol (not shown) to ensure that particles contacting these surfaces were captured. ACI Filter stage 143 is coupled to stage 1 (142). ACI Filter stage 143 includes a glass fiber filter (not shown) for collecting respirable particles, the total mass of collected respirable particles constituting the estimated respirable dose. Tubing 150 couples ACI 140 to Apparatus B (160) and couples vacuum source 170 to Apparatus B (160). Tubing 150 is interrupted by 2-port solenoid valve 161 and flow control valve 162 in Apparatus B (160). Solenoid valve 161 is controlled by timer 163. Although not shown, pressure gauges $P_2$ and $P_3$ are connected with tubing 150, one on each side of flow control valve 162. Opening solenoid valve 161 allows air flow through test dry-powder inhaler 101 and apparatus 100. By adjusting flow control valve 162, a pressure drop of 4 kPa across the dry-powder inhaler is established. The corresponding air flow rate is then measured, which is the target flow rate for determining the respirable dose. Timer 163 is set to open solenoid valve for sufficient time at the target flow rate so that 4 liters of air flows through test dry-powder inhaler 101 and apparatus 100.

Figure 2:
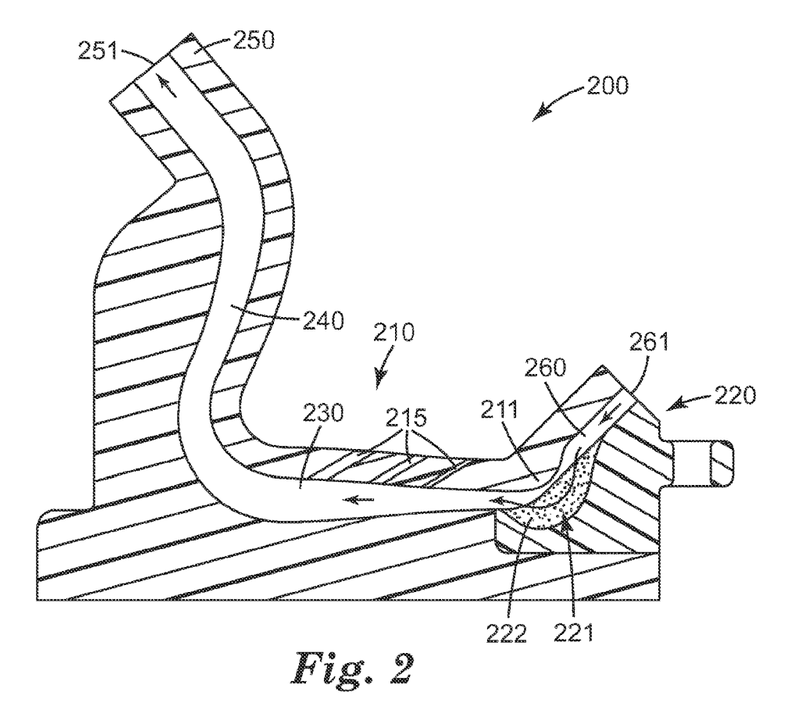
FIG. 2 is a longitudinal cross section through a dry-powder inhaler comprising a conventional reservoir.

In FIG. 2, dry-powder inhaler 200 includes housing 210 and conventional reservoir body 220. Housing 210 includes air passage 230 which transitions into S-bend deagglomerator channel 240 terminating in mouthpiece 250 with outlet 251. Conventional reservoir body 220 includes powder well 221 and when coupled with housing 210 forms air passage 260 with air inlet 261. Air entering inlet 261 passes through air passage 260, striking powdered medicament 222 in well 221, very rapidly entraining the powder, then passes through air passage 230 and S-bend dagglomerator channel 240, and then exits mouthpiece 250 at outlet 251. The flow of air through inhaler 200 is represented by the arrows in inlet 261, passages 260 and 230, reservoir 221, and outlet 251. Here the air passing through the device does not travel substantially parallel to an upper surface of the reservoir and powdered medicament positioned on the base in the reservoir, but rather is direct into the reservoir and into the powder in the reservoir. Housing element 211 diverts air entering inlet 261 and passage 260 so as to impinge upon powdered medicament 222 as shown by the arrow from passage 260 through reservoir 221. Auxiliary air inlets 215 are optionally provided to further dilute the entrained powdered medicament with more air.

Figure 3:
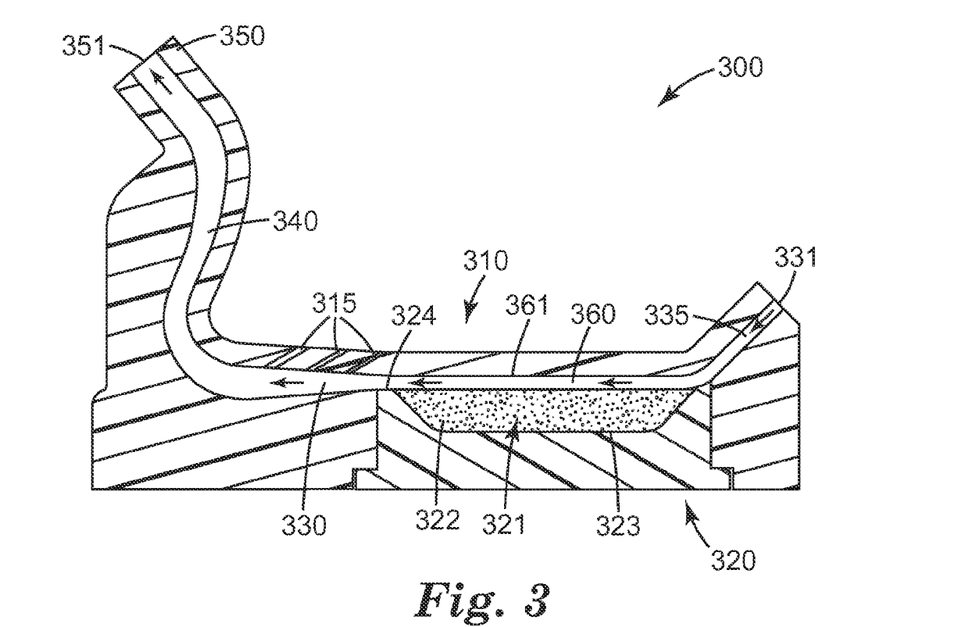
FIG. 3 is a longitudinal cross section through a presently provided dry-powder inhaler comprising the presently provided reservoir.

In FIG. 3, presently provided dry-powder inhaler 300 includes housing 310 and presently provided reservoir body 320. Housing 310 includes air inlet 331, air passage 335, and air passage 330 which transitions into S-bend deagglomerator channel 340 terminating in mouthpiece 350 with outlet 351. Reservoir body 320 includes reservoir 321 with base 323 and when coupled with housing 310 forms air passage 360 which is continuous with air passages 330 and 335. Air passage 360 has top surface 361 which, in certain embodiments, preferably is 1 to 3 mm from upper reservoir surface 324. The width of air passage 360 is at least as wide as the width of reservoir 321. For certain embodiments, preferably air passage 360 is wider than the width of reservoir 321 (e.g., at least 5%, 10%, 20%, 30%, or 40% wider). The width of reservoir 321 is represented by width 425 in FIG. 4B. Air entering inlet 331 passes through air passage 335 and then air passage 360 where the air passes substantially parallel to upper surface 324 of reservoir 321 and substantially parallel to powdered medicament 322 in reservoir 321, entraining the powder over a significantly longer period of time than in the configuration shown in FIG. 2. Air passage 360 in combination with reservoir 321 form a powder chamber through which the air travels as it follows air passage 360. The air passing parallel to or substantially parallel to upper surface 324 of reservoir 321 and powdered medicament 322 is shown by the arrows in air passage 360. For certain embodiments, the powder is entrained over a time period of at least 0.5 seconds, 1 second, 2 seconds, 3 seconds, or up to 4 seconds. For certain embodiments, during an inhalation, the amount of powdered medicament which can be removed from the reservoir during the first 0.5 seconds of air passing through the inhaler is limited to not more than 80% of the total powder removed during the entire inhalation, preferably not more than 60%, more preferably not more than 40%, most preferably not more than 20%. The time period for removing the powder from the reservoir and entraining the powder is preferably determined at a pressure drop of 4 kPa across the dry-powder inhaler. For certain embodiments, this is determined at an air flow rate of at least 50, preferably at least 60 liters per minute using the FDP Apparatus as used in the Examples below. The air then passes through air passage 330 and S-bend dagglomerator channel 340, then exiting mouthpiece 350. Auxiliary air inlets 315 are optionally provided to further dilute the entrained powdered medicament with more air.

Figure 4A:
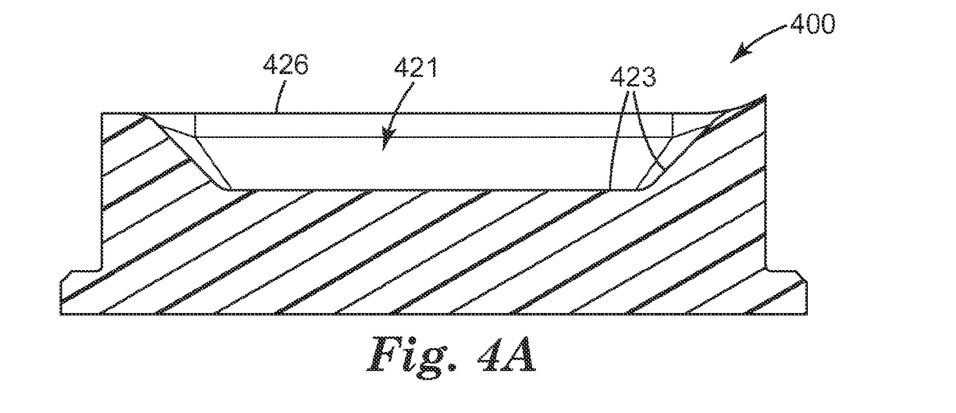
FIG. 4A is a cross-sectional side view of a presently provided reservoir.

In FIG. 4A, presently provided reservoir body 400, corresponding to reservoir body 320 in FIG. 3, is shown in cross-sectional side view separate from housing 310 of FIG. 3. Reservoir body 400 includes reservoir 421, reservoir base 423, and reservoir top edge 426, corresponding to upper reservoir surface 324 in FIG. 3. Reservoir base 421 has a rounded configuration and encompasses all internal surfaces of reservoir 421. All inside corners are, therefore, rounded to minimize or eliminate powder hold-up in the reservoir during an inspiration.

Figure 4B:
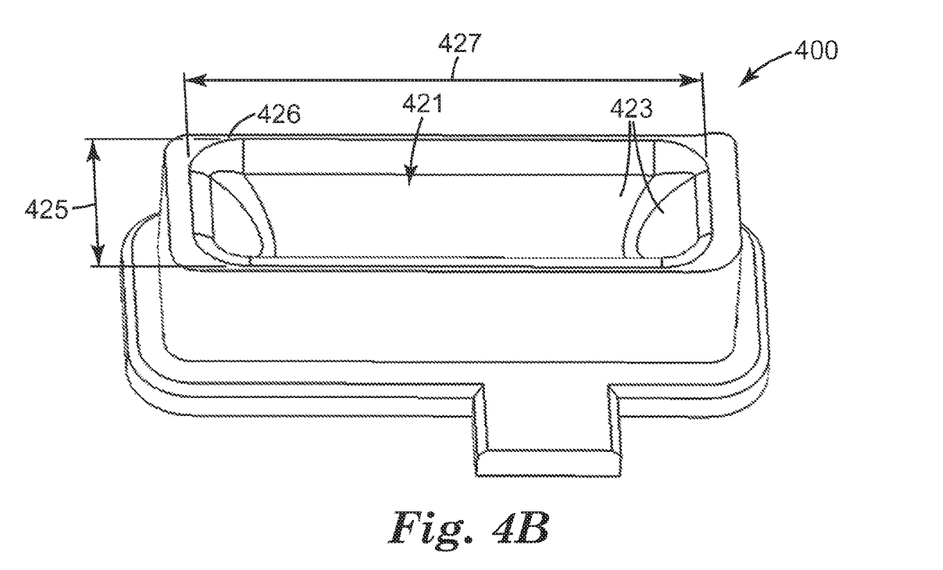
FIG. 4B is a perspective view of the reservoir of FIG. 4A.

In FIG. 4B, reservoir body 400 is shown in a perspective view and includes reservoir 421, base 423, and top edge 426 corresponding to upper reservoir surface 324 in FIG. 3. Reservoir 421 has width 425 and length 427. Length 427 is oriented in the direction of air flow when reservoir body 400 is installed in dry-powder inhaler housing 310. In one example, width 425 is 9.17 mm and 427 is 27.1 mm, resulting in a maximum top surface area in reservoir 421 and maximum exposed surface area of powdered medicament in reservoir 421 of 9.17 mm×27.1 mm=248.5 mm$^2$ (2.48 cm$^2$).

Figure 4C:
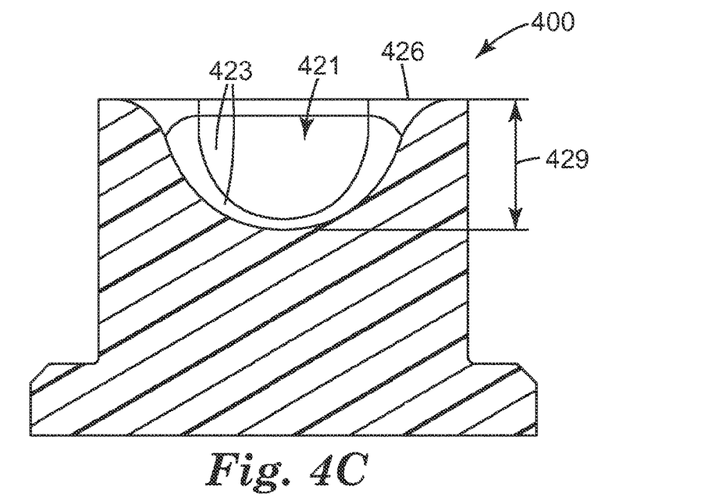
FIG. 4C is a cross-sectional end view of the reservoir of FIG. 4A.

In FIG. 4C, reservoir body 400 is shown in a cross-sectional end view and includes reservoir 421 and base 423. Reservoir 421 has maximum depth 429. In one example, depth 429 is 3.50 mm.

Figure 5:
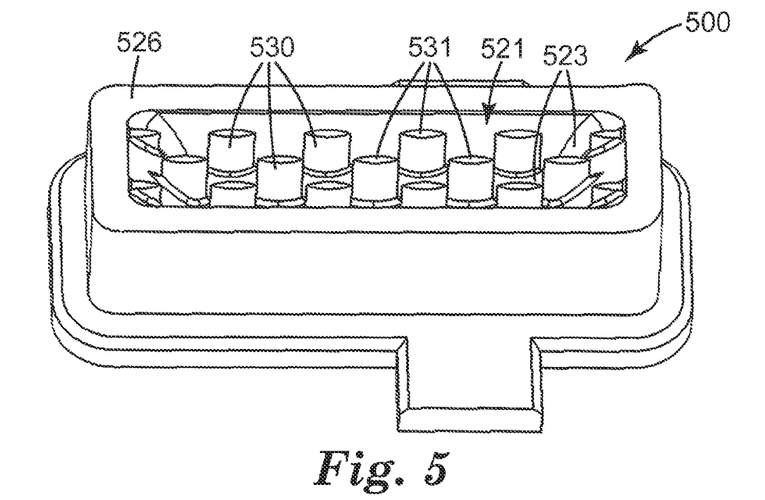
FIG. 5 is a perspective view of a reservoir having a plurality of paddles emerging from the base of the reservoir.

Reservoir body 500 shown in FIG. 5 includes a plurality of paddles 530, only a portion of which are labeled, emerging from base 523 of reservoir 521. Paddles 530 are entrainment-modulating structures as described above. In one example, the width of reservoir 521 is 6.5 mm as described for width 425 in FIG. 4B, the length of reservoir 521 is 26.1 mm as described for length 427 in FIG. 4B, and the depth of reservoir 521 in the center is 3.50 mm as described for depth 429 in FIG. 4C. In this example, the maximum top surface area in reservoir 521 and maximum exposed surface area of powdered medicament in reservoir 521 is 6.5 mm×26.1 mm=170 mm$^2$ (1.70 cm$^2$). Paddle tops 531, only a portion of which are labeled, are, in one example, 0.04 mm below reservoir top edge 526, corresponding to upper reservoir surface 324 in FIG. 3.

Figure 6:
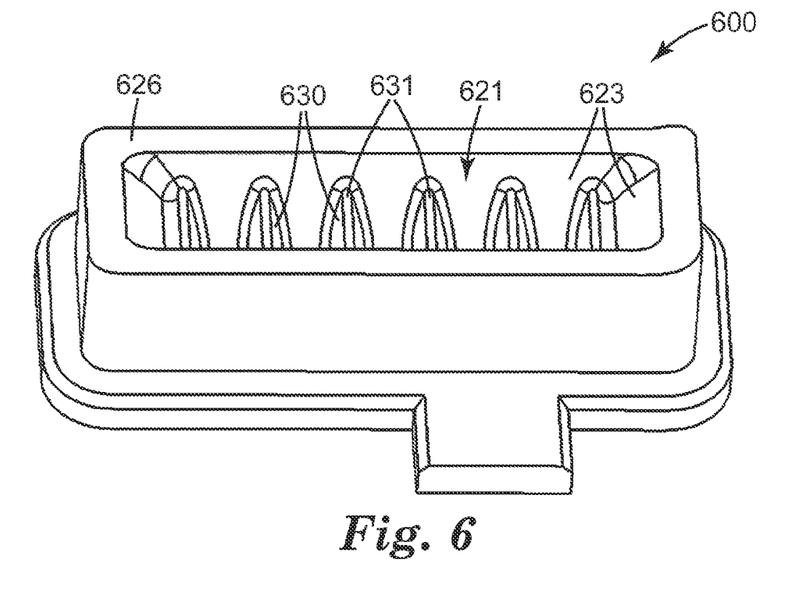
FIG. 6 is a perspective view of a reservoir having a series of baffles emerging from the base of the reservoir.

Reservoir body 600 shown in FIG. 6 includes a plurality of baffles 630, only a portion of which are labeled, emerging from base 623 of reservoir 621. Baffles 630 are entrainment-modulating structures as described above. In one example, the width of reservoir 621 is 6.5 mm as described for width 425 in FIG. 4B, the length of reservoir 621 is 26.1 mm as described for length 427 in FIG. 4B, and the depth of reservoir 621 in the center is 3.45 mm as described for depth 429 in FIG. 4C. In this example, the maximum top surface area in reservoir 621 and maximum exposed surface area of powdered medicament in reservoir 621 is 6.5 mm×26.1 mm=170 mm$^2$ (1.70 cm$^2$). Baffle tops 631, only a portion of which are labeled, are, in one example, 1.86 mm below reservoir top edge 626, corresponding to upper reservoir surface 324 in FIG. 3.

Figure 7:
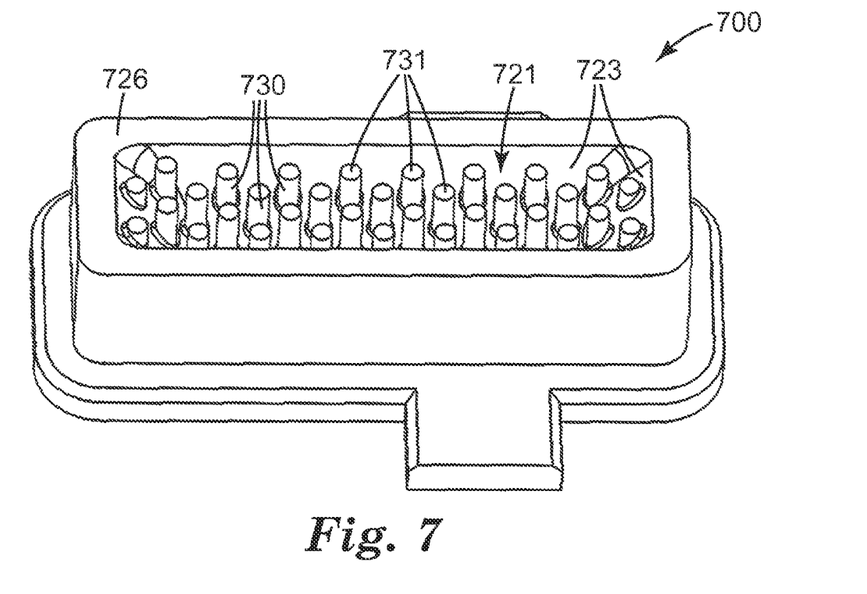
FIG. 7 is perspective view of a reservoir having a plurality of posts emerging from the base of the reservoir.

Reservoir body 700 shown in FIG. 7 includes a plurality of posts 730, only a portion of which are labeled, emerging from base 723 of reservoir 721. Posts 730 are entrainment-modulating structures as described above. In one example, the width of reservoir 721 is 6.5 mm as described for width 425 in FIG. 4B, the length of reservoir 721 is 26.1 mm as described for length 427 in FIG. 4B, and the depth of reservoir 721 in the center is 3.50 mm as described for depth 429 in FIG. 4C. In this example, the maximum top surface area in reservoir 721 and maximum exposed surface area of powdered medicament in reservoir 721 is 6.5 mm×26.1 mm=170 mm$^2$ (1.70 cm$^2$). Post tops 731, only a portion of which are labeled, are, in one example, 0.04 mm below reservoir top edge 726, corresponding to upper reservoir surface 324 in FIG. 3.

Figure 8:
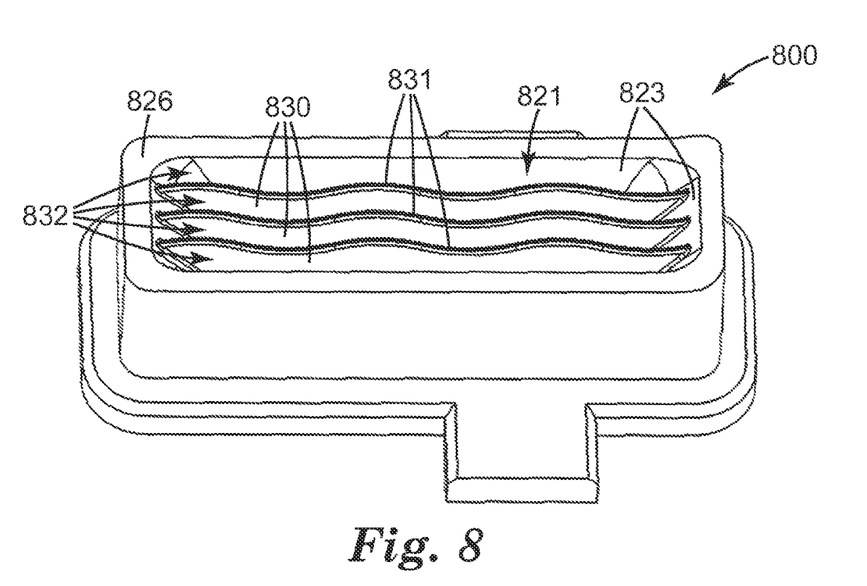
FIG. 8 is a perspective view of a reservoir having a plurality walls running parallel to the long axis of the reservoir.

Reservoir body 800 shown in FIG. 8 includes a plurality of ridges (walls) 830 defining channels 832. Ridges 830 and channels 832 are parallel to the long axis of reservoir 821 and parallel to air flow when installed within the dry-powder inhaler. Ridges 830 and channels 832 are curved. The ridges emerge from base 823 of reservoir 821. Ridges 830 and channels 832 are entrainment-modulating structures as described above. In one example, the width of reservoir 821 is 7.25 mm as described for width 425 in FIG. 4B, the length of reservoir 821 is 26.4 mm as described for length 427 in FIG. 4B, and the depth of reservoir 821 in the center is 3.71 mm as described for depth 429 in FIG. 4C. In this example, the maximum top surface area in reservoir 821 and maximum exposed surface area of powdered medicament in reservoir 821 is 7.25 mm×26.4 mm=191 mm$^2$ (1.91 cm$^2$). Ridge tops 831 are, in one example, 0.25 mm below reservoir top edge 826, corresponding to upper reservoir surface 324 in FIG. 3.

The present disclosure also provides a method of delivering a single high respirable dose of a powdered medicament to a patient. The method includes providing a dry-powder inhaler including any one or combination of the embodiments described herein. The method further includes having a patient inhale through the mouthpiece of the dry-powder inhaler; wherein the patient receives a respirable dose of at least 5 mg, preferably at least 10 mg of powdered medicament. Preferably, the patient receives a respirable dose of not more than 100 mg, 75 mg, 60 mg, 50 mg, 40 mg, 35 mg, 25 mg, or 20 mg of powdered medicament. For certain of these embodiments, preferably during an inhalation the amount of powdered medicament which is removed from the reservoir during the first 0.5 seconds of air passing through the inhaler is limited to not more than 80% of the total powder removed during the entire inhalation, preferably not more than 60%, more preferably not more than 40%, most preferably not more than 20%. For certain of these embodiments, these limits are achieved during the first 1 second of air passing through the inhaler.

Objects and advantages of this invention are further illustrated by the following examples, but the particular materials, configurations, and values recited in these examples, as well as other conditions and details, should not be construed to unduly limit this invention.

EXAMPLES

Fine Particle Dose Estimation Apparatus (FPD Apparatus)

The FPD Apparatus is shown in FIG. 1 and also described above. The test dry-powder inhaler was coupled to the USP inlet (USP (2005), 601 "Aerosols," USP 28/NF 23, United States Pharmacopeial Convention, Inc., Rockville, Md.). The USP inlet was placed onto a modified Andersen Mark-II Cascade Impactor (ACI; Thermo-Anderson; Smyrna, Ga.) using the 60 liters per minute (lpm) pre-separator stage instead of the inlet cone. The pre-separator was used to collect the large particles delivered from the device. A modified ACI Stage 0 of the ACI was directly under the pre-separator. The Stage 0 was modified by taking a commercial Stage 0 and machining out the interior thin portion of the stage that contains all of the impaction nozzles such that the stage merely had an external shell which allowed coupling of the pre-separator and Stage 1. No impaction plate was placed under the machined out Stage 0. In this way, air passing the pre-separator flowed directly to the nozzles of Stage 1 in order to minimize loss of drug on the internal surfaces of the impactor prior to Stage 1. An impaction plate was placed under Stage 1 to collect the large particles. The fine particle dose (FPD) was the mass of drug collected on the glass fiber filter in the filter stage. Tubing at the bottom of the ACI was coupled to Apparatus B which in turn was connected to a vacuum source using tubing.

Prior to adding powder to the reservoir, the test dry-powder inhaler was coupled to the test apparatus shown in FIG. 1. The solenoid valve was opened such that there was airflow through the system. The flow control valve on Apparatus B was adjusted until the pressure drop across the dry-powder inhaler was 4 kPa and the flow rate was measured. This was the target flow rate for the test. The time required to sample a total of 4 liters at the target flow rate was calculated and the timer was adjusted to open the solenoid valve for this duration during testing. The USP inlet was coated to ensure that particles impacting on the surface were captured. Five drops of a 50:50 glycerol/methanol solution were placed in the inside of the USP inlet and a swab was used to spread the solution such that the interior of the USP inlet was uniformly coated. In a similar manner, the impaction plate under Stage 1 of the ACI was coated using four drops of the same solution. Prior to testing, the mass of a glass fiber filter was recorded and the filter was placed in the Filter stage of the ACI. The powder to be tested was loaded into the reservoir and the mass of powder was recorded. The reservoir was placed into the dry-powder inhaler. The dry-powder inhaler was coupled to the USP inlet and the timer on the Apparatus B was started which allowed air to be drawn through the system at the target flow rate for the prescribed duration. After the timer turned the airflow off, the fine particle dose (FPD) of the drug was gravimetrically determined by determining the weight of the filter and comparing it to the initial weight of the filter.

Comparative Example 1

The powdered medicament delivery from the dry-powder inhaler configuration shown in FIG. 2 was evaluated using micronized albuterol sulfate powder and the FPD Apparatus tested at 70 lpm (4 kPa pressure drop) for 3.4 seconds providing 4 liters of inhalation air. The device utilized an S-bend deagglomerator that breaks down large drug particle agglomerates by high velocity impaction of drug agglomerate particles into the surface of the S-bend. The width of the reservoir was 8.00 mm and the length of the reservoir was 10.00 mm. The reservoir had a length/width aspect ratio of 1.25 (10 mm/8 mm). The surface area of the top of the reservoir was 0.80 cm$^2$. The volume of the reservoir was 0.155 milliliters (ml) (cm$^3$), with a surface/volume ratio of 5.2 cm$^{-1}$. Micronized albuterol sulfate powder (47.6 mg) was loaded into the conventional reservoir and evenly distributed, and the reservoir was positioned on the right side of the dry-powder inhaler as shown in FIG. 2. The FPD delivered from this configuration was 1.9 mg (4.0% of the loaded dose). The entire dry-powder inhaler of FIG. 2 was made from a clear polymeric material allowing visual observation of the powder in the reservoir. The drug was removed from the reservoir in less than 0.2 seconds after the airflow began.

Example 2

The powdered medicament delivery from the dry-powder inhaler configuration shown in FIG. 3 was evaluated using the reservoir design shown in FIGS. 4A, 4B, and 4C. Micronized albuterol sulfate powder and the FPD Apparatus at 62 lpm (4 kPa pressure drop) for 3.9 seconds were used. The dry-powder inhaler directed the air into an airflow path approximately parallel with the top surface of the reservoir. The flow path that was located above the reservoir was 1.30 mm high and 11.99 mm wide. The width of the reservoir at the very top was 9.17 mm and the length of the reservoir was 27.1 mm. The reservoir had a length/width aspect ratio of 2.96 (27.1 mm/9.17 mm). The total surface area of the top of the reservoir was 2.48 cm$^2$. The depth of the reservoir in the center was 3.50 mm. The volume of the reservoir was 350 microliters (mcl) (0.350 cm$^3$), and the surface/volume ratio of the reservoir was 2.48 cm$^2$/0.350 cm$^3$=7.09 cm$^{-1}$. The S-bend deagglomerator used in the dry-powder inhaler of FIG. 3 is identical to the S-bend used in FIG. 2. A total of 66.8 mg of micronized albuterol sulfate powder was loaded into the reservoir and evenly distributed, and the reservoir was positioned on the bottom of the dry-powder inhaler as shown in FIG. 3. The FPD delivered from this configuration was 10.6 mg (15.9% of the loaded dose). The entire dry-powder inhaler of FIG. 3 was made from a clear polymeric material allowing visual observation of the powder in the reservoir. The duration of the drug powder release from the reservoir lasted for more than 0.5 seconds after the start of the airflow.

Example 3

The powdered medicament delivery from the dry-powder inhaler configuration shown in FIG. 3 was evaluated using the reservoir design shown in FIG. 5, micronized albuterol sulfate powder, and the FPD Apparatus at 62 lpm (4 kPa pressure drop) for 3.9 seconds. The width of the reservoir at the very top was 6.5 mm and the length of the reservoir was 26.1 mm. The reservoir had a length/width aspect ratio of 4.02 (26.1 mm/6.5 mm). The total surface area of the top of the reservoir was 1.70 cm$^2$. The depth of the reservoir in the center was 3.50 mm. The volume of the reservoir was 401 mcl (0.401 cm$^3$), and the surface/volume ratio was 1.70 cm$^2$/0.401 cm$^3$=4.24 cm$^{-1}$. The reservoir contained seventeen paddles emerging from the base of the reservoir, with the paddles in staggered rows as shown in FIG. 5. The tops of the paddles were 0.04 mm lower than the top of the reservoir. A total of 63.4 mg of albuterol sulfate powder was loaded into the reservoir and evenly distributed, and the reservoir was positioned on the bottom of the dry-powder inhaler as shown in FIG. 3. The FPD delivered from this configuration was 10.1 mg (15.9% of the loaded dose). The duration of the drug powder release from the reservoir lasted for more than 0.5 seconds after the start of the airflow.

Example 4

The powdered medicament delivery from the dry-powder inhaler configuration shown in FIG. 3 was evaluated using the reservoir design shown in FIG. 6, micronized albuterol sulfate powder, and the FPD Apparatus at 62 lpm (4 kPa pressure drop) for 3.9 seconds. The width of the reservoir at the very top was 6.5 mm and the length of the reservoir was 26.1 mm. The reservoir had a length/width aspect ratio of 4.02 (26.1 mm/6.5 mm). The total surface area of the top of the reservoir was 1.70 cm$^2$. The depth of the reservoir in the center was 3.45 mm. The volume of the reservoir was 363 mcl (0.363 cm$^3$), and the surface/volume ratio was 1.70 cm$^2$/0.363 cm$^3$=4.68 cm$^{-1}$. There were six wedge-shaped ridges or baffles, each extending across the width of the reservoir and emerging from the reservoir base. These baffles were positioned along the length of the reservoir and formed a series of small reservoirs located between the baffles as shown in FIG. 6. The tops of the ridges were 1.86 mm lower than the top of the reservoir. A total of 65.6 mg of albuterol sulfate powder was loaded into the reservoir and evenly distributed, and the reservoir was positioned on the bottom of the dry-powder inhaler as shown in FIG. 3. The FPD delivered from this configuration was 6.7 mg (10.2% of the loaded dose). The duration of the drug powder release from the reservoir lasted for more than 0.5 seconds after the start of the airflow.

Example 5

The powdered medicament delivery from the dry-powder inhaler configuration shown in FIG. 3 was evaluated using the reservoir design shown in FIG. 7, micronized albuterol sulfate powder, and the FPD Apparatus at 62 lpm (4 kPa pressure drop) for 3.9 seconds. The width of the reservoir at the very top was 6.5 mm and the length of the reservoir was 26.1 mm. The reservoir had a length/width aspect ratio of 4.02 (26.1 mm/6.5 mm). The total surface area of the top of the reservoir was 1.70 cm$^2$. The depth of the reservoir in the center was 3.50 mm. The volume of the reservoir was 359 mcl (0.359 cm$^3$), and the surface/volume ratio was 1.70 cm$^2$/0.359 cm$^3$=4.74 cm$^{-1}$. The reservoir contained 34 posts emerging from the reservoir base and positioned in staggered rows as shown in FIG. 7. The tops of the posts were 0.04 mm lower than the top of the reservoir. A total of 60.2 mg of albuterol sulfate powder was loaded into the reservoir and evenly distributed, and the reservoir was positioned on the bottom of the dry-powder inhaler as shown in FIG. 3. The FPD delivered from this configuration was 12.3 mg (20.4% of the loaded dose). The duration of the drug powder release from the reservoir lasted for more than 0.5 seconds after the start of the airflow.

Example 6

The powdered medicament delivery from the dry-powder inhaler configuration shown in FIG. 3 was evaluated using the reservoir design shown in FIG. 8, micronized albuterol sulfate powder, and the FPD Apparatus at 62 lpm (4 kPa pressure drop) for 3.9 seconds. The width of the reservoir at the very top was 7.25 mm and the length of the reservoir was 26.4 mm. The reservoir had a length/width aspect ratio of 3.64 (26.4 mm/7.25 mm). The total surface area of the top of the reservoir was 1.91 cm$^2$. The depth of the reservoir in the center was 3.71 mm. The volume of the reservoir was 375 mcl (0.375 cm$^3$), and the surface/volume ratio was 1.91 cm$^2$/0.375 cm$^3$=5.09 cm$^{-1}$. The reservoir contained three curved ridges running the length of the of the reservoir and defining channels parallel to air flow. The tops of the ridges were 0.25 mm lower than the top of the reservoir. A total of 65.0 mg of albuterol sulfate powder was loaded into the reservoir and evenly distributed, and the reservoir was positioned on the bottom of the dry-powder inhaler as shown in FIG. 3. The FPD delivered from this configuration was 7.8 mg (12.0% of the loaded dose). The duration of the drug powder release from the reservoir lasted for more than 0.5 seconds after the start of the airflow.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dry-powder inhaler comprising:
   a housing comprising at least one air inlet to a first air passage and a second air passage extending from the first air passage and terminating in a mouthpiece; the housing thereby providing a continuous air passage through the at least one air inlet, the first and second air passages, and the mouthpiece;
   a rigid, fixed, powdered-medicament reservoir comprising a base, the reservoir being associated with the first air passage, and together with the first air passage forming a powder chamber;
   wherein air passing through the powder chamber travels substantially parallel to an upper surface of the reservoir and substantially parallel to powdered medicament positioned on the base in the reservoir, the upper surface of the reservoir having a surface area, and the reservoir having a volume, the surface area being at least 1 cm$^2$, and the surface area to volume ratio being at least 1 cm$^{-1}$ and not more than 10 cm$^{-1}$;
   wherein the dry-powder inhaler has a single respirable-dose delivery capability of at least 5 mg of the powdered medicament; and
   wherein the dry-powder inhaler has a plurality of entrainment-modulating structures in contact with the powdered medicament in the reservoir.

2. The dry-powder inhaler of claim 1, wherein the reservoir and powder chamber are elongated along a long axis which is parallel to the flow of air through the first passage; and wherein the reservoir has a length along the long axis and a width perpendicular to the long axis, the length and width defining a length/width aspect ratio of at least 2.5.

3. The dry-powder inhaler of claim 2, wherein the aspect ratio is at least 3.0.

4. The dry-powder inhaler of claim 1, wherein the powdered-medicament reservoir has a volume of 0.1 to 5 ml.

5. The dry-powder inhaler of claim 4, wherein the volume is 0.1 ml to 2.0 ml.

6. The dry-powder inhaler of claim 1, wherein the upper surface of the reservoir is spaced a distance of at least 1 mm and not more than 3 mm from a top surface of the first air passage.

7. The dry-powder inhaler of claim 1, wherein the entrainment-modulating structures emerge from the base of the reservoir.

8. The dry-powder inhaler of claim 7, wherein the entrainment-modulating structures are selected from the group consisting of posts, paddles, baffles, walls parallel to air flow, and a combination thereof.

9. The dry-powder inhaler of claim 1, wherein an amount of powdered medicament which can be removed from the reservoir during a first 0.5 seconds of air passing through the inhaler is limited to not more than 80% of total powdered medicament removed during an entire inhalation.

10. The dry-powder inhaler of claim 1, further comprising a deagglomerator associated with the second air passage, associated with the powder chamber, or associated with both the second air passage and the powder chamber and comprising a portion of the continuous air passage.

11. The dry-powder inhaler of claim 10, wherein the deagglomerator causes deagglomeration of the powder by impacting agglomerates against a surface of the dry-powder inhaler, against other particles contained in the powder, or a combination thereof.

12. The dry-powder inhaler of claim 11, wherein the deagglomerator is a particle-to-surface impaction deagglomerator.

13. The dry-powder inhaler of claim 10, wherein the deagglomerator is an S-shaped channel.

14. The dry-powder inhaler of claim 13, wherein the S-shaped channel has a cross-sectional area that varies along a longitudinal axis of the channel, the cross-sectional area being perpendicular to the longitudinal axis.

15. The dry-powder inhaler of claim 14, wherein the channel includes at least one convergence and one divergence corresponding to a cross-sectional area decrease of about 15 to about 35 percent and a cross-sectional increase of about 15 to about 35 percent, respectively.

16. The dry-powder inhaler of claim 1, wherein the inhaler has a single respirable-dose delivery capability of at least 10 mg of the powdered medicament.

17. The dry-powder inhaler of claim 1, wherein the powdered-medicament reservoir is removable and replaceable.

18. The dry-powder inhaler of claim 1, wherein the powdered-medicament reservoir contains a removable seal covering the powder in the reservoir prior to use.

19. A method of delivering a single high respirable dose of a powdered medicament to a patient, the method comprising the steps of:

providing the dry-powder inhaler of claim 1; and having a patient inhale through the mouthpiece of the inhaler;

wherein the patient receives a respirable dose of at least 5 mg of the powdered medicament.

20. The method of claim 19, where during an inhalation the amount of powdered medicament which is removed from the reservoir during the first 0.5 seconds of air passing through the inhaler is limited to not more than 80% of total powder removed during the entire inhalation.

* * * * *